United States Patent [19]

Hoelderich et al.

[11] Patent Number: 4,616,098

[45] Date of Patent: Oct. 7, 1986

[54] PREPARATION OF OLEFINS FROM METHANOL/DIMETHYL ETHER

[75] Inventors: Wolfgang Hoelderich, Frankenthal; Walter Himmel, Fussgoenheim; Wolf D. Mross, Frankenthal; Matthias Schwarzmann, Limburgerhof, all of Fed. Rep. of Germany

[73] Assignee: BASF Aktiengesellschaft, Ludwigshafen, Fed. Rep. of Germany

[21] Appl. No.: 649,977

[22] Filed: Sep. 12, 1984

Related U.S. Application Data

[63] Continuation-in-part of Ser. No. 478,996, Mar. 25, 1983, abandoned.

[30] Foreign Application Priority Data

Mar. 27, 1982 [DE] Fed. Rep. of Germany ....... 3211399
Jan. 14, 1983 [DE] Fed. Rep. of Germany ....... 3300982

[51] Int. Cl.$^4$ .............................................. C07C 1/20
[52] U.S. Cl. .................................................. 585/640
[58] Field of Search ..................... 585/640, 469, 733

[56] References Cited

U.S. PATENT DOCUMENTS 4,178,317 12/1979 Hern et al. ......................... 585/640
4,268,420 5/1981 Klotz ................................. 585/640
4,292,458 9/1981 Klotz ................................. 585/640

FOREIGN PATENT DOCUMENTS 2615150 4/1976 Fed. Rep. of Germany.

Primary Examiner—William R. Dixon, Jr.
Assistant Examiner—Cynthia A. Prezlock
Attorney, Agent, or Firm—Keil & Weinkauf

[57] ABSTRACT

Olefins are prepared by converting methanol and/or dimethyl ether in the presence of a zeolite catalyst at elevated temperatures by a process wherein the catalyst used is a borosilicate zeolite which has been molded together with an amorphous binder containing aluminum oxide and silicon dioxide. The advantage of using the borosilicate catalyst is that the yield of $C_2$–$C_4$-olefins is improved at the expense of formation of higher hydrocarbons.

9 Claims, No Drawings

PREPARATION OF OLEFINS FROM METHANOL/DIMETHYL ETHER

This application is a continuation-in-part of application Ser. No. 478,996, filed on Mar. 25, 1983, now abandoned.

Recently, efforts to prepare olefins from methanol have become increasingly important. Methanol can be readily produced from coal, via coal gasification and the production of synthesis gas, with the aid of well-tried technology. If it were possible to convert methanol to lower olefins in an economical manner, the further processing methods which are conventional in the chemical industry today and employ coal as a raw material could also be preserved. In the past few years, processes have therefore been developed with the object of preparing olefins from methanol and/or dimethyl ether. Such a process is described in, for example, German Laid-Open Application DOS No. 2,615,150. In this process, the catalyst used is a ZSM-5 aluminosilicate zeolite, which is in fact an aromatization catalyst. However, by means of various measures, in particular by reducing the residence time, the conversion can be steered in the direction of olefin formation. Other factors which favor olefin formation are, in particular, dilution of the methanol and the dimethyl ether with an inert gas and steam, respectively, or dilution of the catalyst with a binder. Experience has shown that high olefin yields are obtainable only when methanol and/or dimethyl ether are very substantially diluted with an inert gas or steam. Other processes which have been disclosed have the disadvantage that the catalyst can be subjected only to a low load and is rapidly coked. However, there is considerable interest in a simple process which would make it possible to achieve complete conversion of crude methanol and/or dimethyl ether to a hydrocarbon mixture predominantly comprising $C_2$-$C_4$-olefins.

We have found that $C_2$-$C_4$-olefins are obtained in high yield by catalytic conversion of methanol and/or dimethyl ether at elevated temperatures, in the presence of a zeolite catalyst, when the catalyst used is a borosilicate zeolite which has been molded together with an amorphous binder containing aluminum oxide and silicon dioxide.

The binder used can be, for example, an amorphous aluminosilicate. Advantageously, it has an $SiO_2/Al_2O_3$ ratio of from 35:65 to 75:25% by weight.

However, it is also possible to use, as the binder, a mixture containing silicon dioxide together with 10% by weight of aluminum dioxide. Advantageously, molding is carried out using a binder mixture consisting of highly dispersed silicon dioxide and highly dispersed aluminum oxide, of highly dispersed silicon dioxide and boehmite, or of silica gel and boehmite. It is advantageous to use a catalyst which has been obtained by molding the borosilicate zeolite with a binder comprising from 90 to 98% by weight of highly dispersed $SiO_2$ and from 10 to 2% by weight of highly dispersed $Al_2O_3$. Other advantageous binders include silica gel and/or pyrogenic silica mixed with 10% by weight of boehmite. For the purposes of the invention, highly dispersed $SiO_2$ and $Al_2O_3$ are oxides which have been prepared from the corresponding halides by pyrolysis.

The specific surface of $SiO_2$ is from 130 to 380 m$^2$/g, measured according to Brunner, Emmet and Teller, that of $Al_2O_3$ is from 100 to 200 m$^2$/g, and that of a mixture of $SiO_2$ and $Al_2O_3$ is from 80 to 170 m$^2$/g.

An essential feature of the invention is that the catalyst must have a residual content of aluminum oxide; the latter is required to initiate the first stage of the reaction, i.e. the dehydration of the methanol to give dimethyl ether. The boron zeolite converted to extrudates with aluminum oxide is a bifunctional catalyst, the aluminum oxide effecting dehydration of the methanol to give dimethyl ether, and the boron zeolite converting this to the desired olefins. When the reaction with methanol is carried out using a borosilicate zeolite which has been converted to extrudates exclusively with silica gel or highly dispersed silica, temperatures above 550° C. have to be employed, or olefines have to be fed in or recycled, or pure dimethyl ether has to be used.

To prepare the catalysts, the borosilicate zeolite and the particular binder or binder mixture are molded together to give tablets or extrudates.

It is an object of the present invention to reduce the amounts of higher aliphatic hydrocarbons in favor of $C_2$-$C_4$-olefins, without decreasing the total hydrocarbon yield.

We have found that this object is achieved by initiating cracking reactions which compete with the C—C linking reactions, take place simultaneously to these and effect selective degradation to give the desired $C_2$-$C_4$-olefins.

Methanol and/or dimethyl ether are converted over boron zeolite catalysts of this type, under a pressure of from atmospheric pressure to about 30 bar and at from 300° to 700° C., preferably from 400° to 550° C. The methanol can contain not more than 90% by weight of water. It is preferable to employ crude methanol as obtained from the synthesis of methanol, and containing about 20% by weight of water. Other lower alcohols may also be admixed to the methanol. The catalyst loading, expressed as WHSV in h$^{-1}$, i.e. g of methanol and/or dimethyl ether per g of catalyst per hour, is advantageously chosen such that highly quantitative conversion of these starting materials takes place, so that separation and recycling problems do not arise. In general, therefore, the WHSV is from 0.5 to 50 h$^{-1}$, preferably from 2 to 15 h$^{-1}$. A particular advantage of the invention is that, using the above boron zeolite catalysts, crude methanol or dimethyl ether can be converted to $C_2$-$C_4$-olefins in the absence of a diluent.

The Examples which follow illustrate the process according to the invention.

EXAMPLE 1

The boron zeolite is synthesized hydrothermally from 64 g of $SiO_2$ (highly dispersed silica), 12.2 g of $H_3BO_3$, and 800 g of an aqueous 1,6-hexanediamine solution (50:50 mixture) at 170° C. under autogenous pressure in a stirred autoclave. The crystalline product is filtered off, washed, dried for 24 hours at 160° C. and calcined for 24 hours at 500° C. This borosilicate zeolite is composed of 94.2% by weight of $SiO_2$ and 2.32% by weight of $B_2O_3$.

This boron zeolite was combined with various binder additives to produce catalysts:

Catalyst A is obtained by extruding the borosilicate zeolite described in Example 1 with boehmite in the ratio 60:40. Drying is carried out at 110° C. for 16 hours, and calcining is carried out at 500° C. for 16 hours. Catalyst A is used as a comparative catalyst; boehmite does not possess any cracking properties.

Catalyst B is obtained by extruding 72 g of the borosilicate zeolite described in Example 1 with 48 g of an amorphous aluminosilicate composed of 65% of $Al_2O_3$ and 35% of $SiO_2$. The molding pressure is about 100 bar, and the 2 mm extrudates are dried at 110° C. for 16 hours and calcined at 500° C. for 16 hours.

Catalyst C is obtained in the same manner as catalyst B. The amorphous aluminosilicate employed is composed of 45% of $Al_2O_3$ and 55% of $SiO_2$.

Catalyst D is obtained in the same manner as catalyst B. The amorphous aluminosilicate employed is composed of 25% of $Al_2O_3$ and 75% of $SiO_2$.

EXAMPLE 2

Crude methanol containing 20% of water is converted quantitatively over catalysts A to D under isothermal conditions, in a tube reactor, at 500° C. and a WHSV of 7.8 h−1. The yields of hydrocarbons are shown in Table 1.

TABLE 1

| Catalyst | A | B | C | D |
| --- | --- | --- | --- | --- |
| $CH_4$ % | 5.5 | 4.2 | 4.8 | 4.5 |
| $C_2H_4$ % | 7.9 | 12.2 | 11.3 | 10.9 |
| $C_2H_6$ % | — | 0.4 | 0.4 | 0.4 |
| $C_3H_6$ % | 30.4 | 32.8 | 33.4 | 34.2 |
| $C_3H_8$ % | 1.6 | 2.1 | 1.4 | 1.4 |
| $C_4$ % | 16.8 | 20.5 | 20.3 | 20.8 |
| $C_5^+$ % | 34.5 | 25.5 | 26.2 | 25.5 |
| Time-on-stream (hours)+ | 10 | 14 | 14 | 17 |
| g of $CH_3OH$/g of catalyst | 78 | 109 | 109 | 133 |

+Time-on-stream until the 1st regeneration

EXAMPLE 3

Catalyst A (according to the invention)

The boron zeolite is synthesized hydrothermally from 64 g of $SiO_2$ (highly dispersed silica), 12.2 g of $H_3BO_3$, and 800 g of an aqueous 1,6-hexanediamine solution (50:50 mixture) at 170° C. under autogenous pressure in a stirred autoclave. The crystalline product is filtered off, washed, dried for 24 hours at 110° C. and calcined for 24 hours at 500° C. This borosilicate zeolite is composed of 94.2% by weight of $SiO_2$ and 2.32% by weight of $B_2O_3$.

60 g of this borosillicate zeolite together with 36.5 g of highly dispersed $SiO_2$ and 3.5 g of highly dispersed $Al_2O_3$ are converted to 2 mm extrudates under a molding pressure of 70 bar. The extrudates are dried at 110° C. for 16 hours and calcined at 500° C. for 16 hours.

Catalyst B (according to the invention)

Catalyst B is obtained in the same manner as catalyst A, except that 30 g of highly dispersed $SiO_2$ and 10 g of boehmite are employed as the binder.

Catalyst C (according to the invention)

Catalyst C is prepared in the same manner as catalysts A and B, except that 30 g of silica gel and 10 g of boehmite are used as the binder.

Crude methanol containing 20% by weight of water is converted quantitatively over catalysts A, B and C under isothermal conditions, in a tube reactor, at 550° C. and a WHSV of 7.8 h−1, based on $CH_3OH$ employed. The yields, based on $CH_2$ employed, are shown in Table 2, columns A, B and C.

For comparison of the yields, the catalyst below was employed under the same reaction conditions as those used for catalysts A, B and C.

Catalyst D

Catalyst D is obtained by extruding the above borosilicate zeolite with boehmite in the ratio 60:40. Drying is carried out at 110° C. for 16 hours and calcining is carried out at 500° C. for 16 hours.

TABLE 2

| Catalyst | A | B | C | D |
| --- | --- | --- | --- | --- |
| $C_2H_4$ % | 11.3 | 10.7 | 7.4 | 12.0 |
| $C_3H_6$ % | 42.6 | 39.8 | 39.5 | 32.9 |
| $C_4H_8$ % | 23.1 | 20.7 | 20.1 | 16.1 |
| $CH_4$ % | 1.5 | 3.6 | 2.6 | 7.9 |
| $C_2H_6$ % | 0.3 | 0.6 | 0.3 | 0.6 |
| $C_3H_8$ % | 1.7 | 1.9 | 1.8 | 2.1 |
| $C_4H_{10}$ % | 1.1 | 1.3 | 1.2 | 1.2 |
| $C_5+$-aliphatics | 12.2 | 10.5 | 15.0 | 9.4 |
| $C_6+$-aromatics | 4.1 | 8.9 | 10.2 | 15.9 |
| Time-on-stream (hours)* | 15 | 10 | 10 | 7 |
| g $CH_3OH$/g catalyst | 117 | 78 | 78 | 55 |

*Time-on-stream until the 1st regeneration.

We claim:

1. A process for the preparation of olefins by converting methanol and/or dimethyl ether in the presence of a zeolite catalyst at elevated temperatures, wherein the catalyst used is a borosilicate zeolite which has been molded together with an amorphous binder containing aluminum oxide and silicon dioxide wherein said binder is selected from aluminum silicate or a mixture of highly dispersed silicon dioxide and highly dispersed aluminum oxide.

2. The process of claim 1, wherein a catalyst is used in which an $SiO_2/Al_2O_3$ ratio of from 35:65 to 75:25% by weight is maintained in the binder.

3. A process for the preparation of lower olefins by converting methanol and/or dimethyl ether in the presence of a borosilicate zeolite catalyst at elevated temperatures, which has been molded together with an amorphous binder of silicon dioxide and aluminum dioxide, the aluminum dioxide content being $\leq 10\%$ by weight, or with an amorphous aluminum silicate binder in which a $SiO_2/Al_2O_3$ ratio of from 35:65 to 75:25% by weight is maintained.

4. A process for the preparation of olefins by converting methanol and/or dimethyl ether in the presence of a zeolite catalyst at elevated temperatures, wherein the catalyst used is a borosilicate zeolite which has been molded together with, as an amorphous binder, aluminum silicate in which a $SiO_2/Al_2O_3$ ratio of from 35:65 to 75:25% by weight is maintained.

5. A process for the preparation of olefins by converting methanol and/or dimethyl ether in the presence of a zeolite catalyst at elevated temperatures, wherein the catalyst used is a borosilicate zeolite which has been molded together with an amorphous binder containing a mixture of silicon dioxide and aluminum oxide, the aluminum oxide content being $\leq 10\%$ by weight.

6. The process of claim 5, wherein the amorphous binder comprises from 90 to 98% by weight of highly dispersed silicon dioxide and from 10 to 20% by weight of highly dispersed aluminum oxide.

7. The process of claim 5, wherein a binder mixture of highly dispersed silicon dioxide and highly dispersed aluminum oxide is used for the molding.

8. The process of claim 5, wherein a binder mixture of highly dispersed silicon dioxide and boehmite is used for the molding.

9. The process of claim 5, wherein a binder mixture of silica gel and boehmite is used for the molding.

* * * * *

UNITED STATES PATENT AND TRADEMARK OFFICE
CERTIFICATE OF CORRECTION

PATENT NO. : 4,616,098
DATED : October 7, 1986
INVENTOR(S) : Wolfgang HOELDERICH et al.

It is certified that error appears in the above-identified patent and that said Letters Patent is hereby corrected as shown below:

IN THE CLAIMS:

Claim 6, column 4, line 58, change "10 to 20%" to --10 to 2%--.

Signed and Sealed this

Thirteenth Day of January, 1987

Attest:

DONALD J. QUIGG

Attesting Officer

Commissioner of Patents and Trademarks